United States Patent
Burkhardt et al.

(12)

(10) Patent No.: US 6,342,231 B1
(45) Date of Patent: *Jan. 29, 2002

(54) HAEMOPHILUS PARASUIS VACCINE AND DIAGNOSTIC

(75) Inventors: Douglas T. Burkhardt, Waukee; Karen L. Lenz, West Des Moines, both of IA (US)

(73) Assignee: Akzo Nobel N.V., Arnhem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/108,438

(22) Filed: Jul. 1, 1998

(51) Int. Cl.$^7$ ................... A61K 39/102; A61K 39/02; A61K 39/00; A61K 38/00; C07K 1/00

(52) U.S. Cl. .................. 424/256.1; 424/234.1; 424/236.1; 424/184.1; 514/2; 530/350; 530/825; 530/806; 435/975; 435/7.2

(58) Field of Search .......... 424/256.1, 234.1, 424/186.1, 823, 824, 825, 826, 236.1; 514/2; 435/7.1, 975, 820, 961, 259, 261; 530/412, 350, 806, 825, 820

(56) References Cited

U.S. PATENT DOCUMENTS

| | | | | | |
|---|---|---|---|---|---|
| 5,456,914 A | * | 10/1995 | Stine et al. | .............. | 424/256.1 |
| 5,534,256 A | * | 7/1996 | Potter et al. | ............. | 424/184.1 |
| 5,538,733 A | * | 7/1996 | Emery et al. | ............... | 424/422 |
| 5,648,081 A | | 7/1997 | van den Bosch | ........ | 424/255.1 |
| 5,858,677 A | * | 1/1999 | Forsgren | ....................... | 435/6 |

FOREIGN PATENT DOCUMENTS

| | | | |
|---|---|---|---|
| WO | wo 91/18627 | * | 12/1991 |
| WO | WO 91/18926 | | 12/1991 |

OTHER PUBLICATIONS

Rapp–Gabrielson et al. H. parasuis: Immunogenicity and cross–protection between different serovars. In: Proceedings of the American Association of Swine Practitioners, pp. 26–28, 1994.*
Reddy et al. Anal. Biochem. 214: 106–115, 1993.*
Simpson et al. Methods in Enzymol. 165: 76–85, 1988.*
Dasgupta et al. Toxicon 21: 535–545, 1983.*
Niven DF. Can. J. Microbiol. 30: 763–773, 1984.*
Hartmann et al. J. Vet. Med. B 42: 59–63, 1995.*
Charland et al. Can. J. Microbiol. 41: 70–74, 1995.*
Zucker et al. Am. J. Vet. Res. 57: 63–67, 1996.*
Nielsen et al. Nord. Vet. Med. 27: 20–25, 1975.*
Kielstein et al. J. Vet Med. B 38: 315–320, 1991.*
Rapp–Gabrielson et al. In: Proc. 14th International Pif Veterinary Society Congress, IPVS, Bologna, Italy, Jul. 7–10, p. 300 (cited as reference A), 1996.*
Sidorov et al. Soviet Agric. Sci. 8: 44–45, 1980.*
Rapp et al. In: Abstracts of papers presented at the 66th Annual Meeting of the Conference of Research Workers in Animal Disease, Chicago, Illinois, Nov., pp. 45, abstract 245, 1985.*
Hill et al. Agri–Practice 14: 6–9, 1993.*
Solano–Aguilar et al. Am. J. Vet. Res. 60: 81–87, abstract, 1999.*
Awad–Masalmeh et al. In: Proc. 11th Congr. Inter. Pig Vet. Soc. Lausanne, Switzerland, Jul. 1–5, p. 107, 1990.*
Bhatia et al. Vet. Microbiol. 29: 147–158, abstract, 1991.*
Zucker et al. Berliner und Munchener Ticrarztliche Wochenschrift 107: 78–81, abstract, 1994.*
Morton et al. Dissert. Abstr. Inter. vol. 5108B, 1–53, p. 3675, abstract, 1989.*
Weiss et al. J. Vet. Med. Ser. B 34: 109–118, abstract, 1987.*
Neilsen. Acta Veter. Scand. 34: 193–198, 1993.*
Jayappa et al. In: The 29th Annual Meeting of the American Association of Swine Practitioners, AASP, Des Moines, Iowa, pp. 251–254, 1998.*
Rapp–Gabrielson et al. In: Proc. 13th International Pig Veterinary Society Congress, IPVS, Bangkok, Thailand, p. 157, 1994.*
Morton et al. FEMS Mocrobiol. Lett. 65: 123–128, 1989.*
Hikoo et al. Kachiku. Eisei Kenkyu Kaiho (Bull. Animal Hyg.) 35: 7–11, abstract, 1992.*
Akkoyunlu et al: "Distribution of Protein D, an Immunoglobulin D–Binding, Protein, in Haemophilus Strains." Infection and Immunity (Apr. 1991):59 (4):1231–1238.
Morozumi et al: "Some Antigenic Properties of *Haemophilus parasuis* and a Proposal for Serological Classification." Journal of Clinical Micribiology (Jun. 1986): 23(6): 1022–1025.
Amano et al: "Effects on Endotoxin Pathogenicity in Pigs with Acute Septicemia of *Haemophilus parasuis* Infection" Institute of Animal Health (Jun. 1997): 59(6): 451–455.
Neumann and Hinz : Elecktrophoretische Auftrennung von Haemophilus–Proteinen im Polyacrylamid–Gel (Polyacrylamid–Gel–Electrophoresis of Haemophilus Proteins) (Jun. 1977): 238(2) : 244–250.
O. Miniats et al., *Can J Vet Res*, 55:33–36, 1991.
O. Miniats et al., *Can J Vet Res*, 55:37–41, 1991.
H. Amano et al., *J. Vet. Med. Sci.*, 59(6):451–455, 1997.
V. Rapp–Gabrielson et al., *Veterinary Medicine*, Jan. 1997, 83–90.
D. Hoefling, *Swine Health and Production*, 2:1:19, 1994.
D. Trott et al., *Proceedings of the 14th IPVS Congress*, Jul. 1996.
V. Rapp–Gabrielson et al., *Am J Vet Res*, 53:5:659–664, 1992.
P. Kielstein et al., *Journal of Clincal Microbiology*, 30:4:862–865, 1992.
J. Nicolet, *Dieseases of Swine*, 7th ed., pp 526–527, 1992.

(List continued on next page.)

*Primary Examiner*—S. Devi
(74) *Attorney, Agent, or Firm*—Michael G. Sullivan

(57) ABSTRACT

A cellfree extract of *Haemophilus parasuis* that exhibits toxic activity is described. The cellfree extract is useful as a vaccine or diagnostic reagent.

8 Claims, 1 Drawing Sheet

OTHER PUBLICATIONS

H. Amano et al., *J. Vet. Med. Sci.*, 56(4): 639–644, 1994.

E. Kamp et al., *Infection and Immunity*, 65:10:4350–4354, 1997.

J. Vahle, Thesis, "Pathogenesis of *Haemophilus parasuis* Infection in Swine" Iowa State University, 1996, 1–107.

* cited by examiner

HAEMOPHILUS PARASUIS VACCINE AND DIAGNOSTIC

FIELD OF THE INVENTION

The invention relates to a cellfree extract preparation of *Haemophilus parasuis*, which has toxic activity. The preparation is useful as a vaccine and as a diagnostic agent for *Haemophilus parasuis*.

BACKGROUND OF THE INVENTION

Glässer observed in 1910 a small Gram-negative organism associated with a fibrinous serositis and polyarthritis in swine, which was eventually identified as *H. parasuis* and distinguished taxonomically from *H. suis*. It is now accepted that *H. parasuis* is the infectious agent of porcine polyserositis and arthritis (or Glasser's disease).

*H. parasuis* (Hps) is a small pleomorphic Gram-negative rod, varying from a coccobacillary form to slender filaments. Growth is supported only on media containing nicotinamide-adenine dinucleotide (NAD) (heated blood agar, Levinthal agar) or on blood agar in the vicinity of a streak of a Staphylococcus strain (satellitism). Visible growth occurs generally after 36–48 hours incubation.

Porcine polyserositis-arthritis is found worldwide and was historically considered to be a sporadic stress-associated disease of young pigs. More recently, introduction of the pathogen into large populations of specific pathogen free (SPF) herds has shown a devastating effect: infection may spread as a contagious disease of high morbidity, affecting pigs of all ages without obvious associated stress factors. The disease most often affects young pigs (2 weeks to 4 months), principally after the weaning period (5–8 weeks). Mortality may reach 50%.

Serological studies using extracts from autoclaved cells with an agar-gel precipitation test have shown at least fifteen distinct serotypes that differ in their pathogenicity (Kielstein, *J. Clin. Micro.* 30:4:862, (1992)).

Vaccines for *H. parasuis* are commercially available, which are made of inactivated bacteria, or bacterins. A disadvantage of bacterin vaccines is that they elicit antibodies against primarily (lipo)polysaccharides that are only specific for a certain serotype of *H. parasuis* and hence are not protective against other *H. parasuis* serotypes. The degree of protection against field infection afforded by bacterin vaccines may also be lower than desired.

Even though not currently available, live attenuated *H. parasuis* vaccines would suffer from the drawbacks normally associated with live vacines, including the risk of inoculating animals with inadequately attenuated pathogens and the possibility that the attenuated bacteria may revert to a pathogenic state resulting in disease in the inoculated animal and spread of the pathogens to other animals.

Thus, there is a need for a *H. parasuis* vaccine which is safe, effective and provides heterologous protection (serotype independent). To this end, the present inventors endeavored to develop an alternative vaccine.

The rapid onset of disease and severity of internal damage suggest that the clinical effects may be caused by the expression of one or more Hps toxin(s). It has been suggested that Hps may induce functional and structural damage to the nasal mucosa by initially associating with the mucous layer and inducing damage to the underlying mucosa by release of one or more toxic compounds (Vahle, J. L., Ph.D. thesis, AAI9626072, 960902, Iowa State University (1996)). The chemical nature of any such toxins and how they exerted their effects was not elucidated.

Gram-negative endotoxin has been studied as a possible virulence factor of *H. parasuis*. Endotoxin is a lipopolysaccharide (LPS) component of the outer membrane of Gram-negative bacteria and is released with bacterial lysis. The study of Amano et al (*J. Vet. Med. Sci.* Vol. 59, No. 6, 451–455 (1997)) reported that Gram-negative endotoxin levels increased in the blood of pigs with acute septicemia caused by *H. parasuis*, and that *H. parasuis* antigen was found associated with pathological lesions. However, one cannot conclude on the basis of the findings of Amano et al. that it is the endotoxin that is causing the clinical and pathological manifestations of the disease, and the identity of the factor(s) causing the pathological effects of *H. parasuis* infection remains unclear.

It is an object of the present invention to find one or more toxins that contribute to the pathology of *H. parasuis* infection. It is also an object of the present invention to develop vaccines containing the one or more toxins. Finally, it is an object of this invention to use this antigenic material as a reagent in a diagnostic test.

SUMMARY OF THE INVENTION

The present invention provides a novel cellfree extract of *Hemophilus parasuis*, which has toxic activity. This extract causes pathological lesions characteristic of *H. parasuis* infection when administered intraperitoneally to pigs. Thus, the extract appears to contain at least one toxin, which is termed herein HpTx. It is also contemplated that there may be more than one toxin in this extract.

Also provided are vaccines containing the extract, which are effective in providing protection against homologous and heterologous challenge. It is contemplated that vaccines containing the isolated toxin or toxins as the immunogen(s) will provide this same type of protection.

Finally, the extract is useful as a diagnostic tool, and can be used to raise antibodies that can be used as diagnostic reagents to detect *H. parasuis* antigen, or could be used itself as a diagnostic reagent to detect antibodies to *H. parasuis*. Kits for diagnostic tests using these materials are also considered part of the present invention.

DETAILED DESCRIPTION OF THE INVENTION

Figure 1:
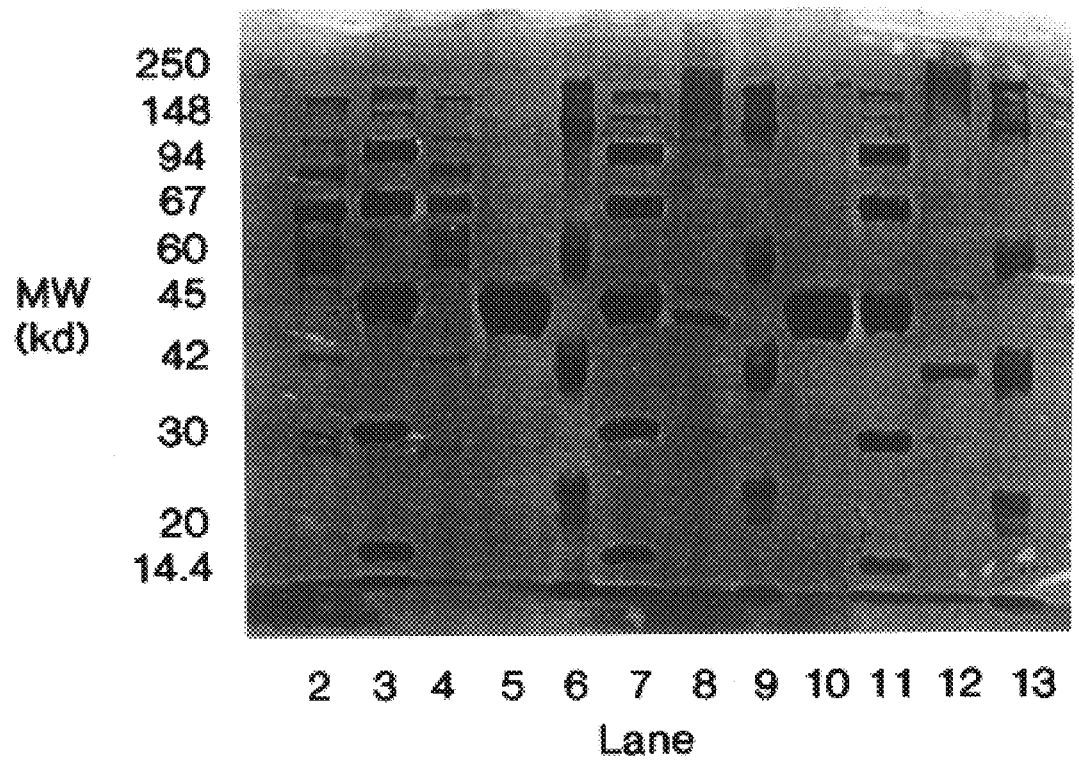
FIG. 1 shows the results of SDS-polyacrylamide gel electrophoresis (SDS-PAGE) of a cell free extract prepared in Example 1 (Preparation C) along with purified outer membrane proteins (OMPs) of serotypes 4 and 5.

The cellfree extract of the present invention is essentially prepared by lysing the bacterial cells, pelleting leftover cells and large cell debris, and collecting the supernatant. The bacterial cells may be lysed by any conventional method; preferably, high pressure is used, such as passing through a microfluidizer. Preferably, the bacterial culture is concentrated prior to lysing, by centrifugation and resuspension of the cell pellet in a smaller volume of fluid than originally present.

Any serotype or strain of *H. parasuis* may be used to prepare the cellfree extract of the present invention. Preferred are serotypes 4 and 5; most preferred is serotype 4.

Preferably, the supernatant containing the cellfree extract is filtered to remove any remaining cells or debris, and this is preferably done using a 0.2 micron filter. The supernatant may be frozen for future use. It is also possible to freeze-dry the cellfree extract and reconstitute the lyophilized material just prior to use.

For parenteral administration, the supernatant material itself may be used as a vaccine formulation or may be admixed with an appropriate pharmaceutical carrier as desired. Lyophilized material is reconstituted in a pharmaceutically suitable carrier, such as an aqueous medium or a water-containing suspension. These carriers are often mixed with other constituents, for example, in order to increase the immunizing activity or shelf life. These consituents may be salts, pH buffers, stabilizers, emulsifiers, and adjuvants to improve the immune response. Examples of adjuvants, without intending to be limiting, include oil-in-water and water-in-oil emulsions, Vitamin E and other tocols, mineral oils, metabolizable organic oils, aluminum compounds, muramyl dipeptide, saponins, polyanions, amphipathic compounds, metal salts, and block (co)polymers. The use of adjuvants is not necessary, however, to provide immunogenic activity to the compositions of the present invention.

The immunogenic preparations of the invention are preferentially administered to swine parenterally, generally by intramuscular or subcutaneous injection. The vaccine is most effective if administered in a series of at least two doses separated by two to three week intervals, but other immunization schedules may be efficacious and may be determined by conventional means.

The amount of cellfree extract preparation used is the amount that is capable of inducing immunity in swine against challenge by *H. parasuis*. Immunity is defined as the induction of a significant level of protection in a population of swine after vaccination compared with an unvaccinated group. On a per dose basis, the quantity of the cellfree extract in a vaccine dose can range from 10 micrograms of protein to about 10 milligrams of protein per pig. A preferable range is from about 1 milligram to about 5 milligrams per pig. One skilled in the art can readily determine the appropriate dose, usually according to the age of the pig.

The vaccines of the present invention may also be formulated into multivalent vaccines comprising other immunogenic materials from one or more other pathogens. For example, the vaccine may contain material from one or more of the following pathogens: pseudorabies virus, transmissible gastroenteritis virus, porcine parvovirus, swine influenza virus, *Mycoplasma hyopneumoniae*, *Escherichia coli*, *Erysipelothrix rhusiopathiae*, *Bordetella bronchioseptica*, *Pasteurella multocida*, and *Actinobacillus pleuropneumonia*.

In a further embodiment of the present invention, the cellfree extract of the invention may be used as a diagnostic tool to detect infection by *H. parasuis*. For instance, the cellfree extract may be used as antigen in an immunological test for *H. parasuis* antibodies in a test sample (tissue or body fluid, e.g. blood, plasma, serum, etc.). Alternatively, the cellfree extract can be used to raise antibodies (monoclonal or polyclonal) to the antigenic material, and the antibody or antibodies can in turn be used in an immunological test for antigen in the test sample. Any immunological test format is contemplated, such as ELISA, Western blot, sandwich assay, etc., which are well known to those skilled in the art. Diagnostic test kits are also embodied in the present invention, and may comprise one or both of cellfree extract and antibodies thereto, optionally bound to a solid support and optionally containing the various reagents (buffers, etc.) used in the test. Detectable labels for the antigen and antibody are well known in the art.

The compositions and methods of the present invention are illustrated by the following non-limiting examples.

EXAMPLES

Example 1

Method of Preparation of Cellfree Extract

Culture Conditions

*H. parasuis* serotype 4, strain SW124, was grown in Tryptic Soy Broth containing 0.1% NAD and 1% yeast extract (H-TSB) with 5% horse serum in 3000 ml total volume. The culture was grown at 37° C. for 5 hours, to about $1 \times 10^8 - 1 \times 10^9$ CFU/ml.

Preparation A

After the above incubation, 250 ml of the culture was harvested by centrifugation at 6000 rpm for 15 minutes to separate out the cells. The supernatant was filtered with a $0.2\mu$ filter (Nalgene). This is a supernatant preparation that would contain any exotoxin(s) and other secreted materials, and is used for comparison purposes.

Preparation B

The remaining portion of the culture (2500 ml) was centrifuged at 6000 rpm for 15 minutes. For this preparation the cells were concentrated by discarding the supernatant and resuspending the pellet with saline to a volume of approximately 300 ml.

The concentrated cells were then lysed with a single pass through a microfluidizer (Microfluidics, Newton, Mass.) at 16,000 psi. The lysed cells were then centrifuged at 8000 rpm for 20 minutes to remove cell debris. The supernatant of this run was then collected and filtered with a $0.2\mu$ filter to remove any remaining cells or large cellular debris. This is a cellfree extract preparation that has toxic activity.

Preparation C

In a preferred method of preparing the cellfree extract, *Haemophilus parasuis* serotype 4, strain SW124, is grown at 37° C. in H-TSB for 3–5 hours to approximately 30% T ($1 \times 10^8 - 1 \times 10^9$ CFU/ml). The culture is centrifuged at 8500×g for 20 minutes. The cell pellet is resuspended in sufficient saline equivalent to a 10-fold concentration of the cells originally present. The cell concentrate is microfluidized at approximately 16,000 psi. Large cell debris is removed by centrifugation at 15,000×g for 20 minutes. The supernatant is filtered through a 0.2 $\mu$m filter. This filtrate can be used as a fresh preparation, but may also be frozen or lyophilized for future use. Storage is at about −70° C.

Example 2

Testing of Biological Activity in Pigs

The preparations of Example 1 were then used to assess biological activity in pigs. Three pigs were inoculated intraperitoneally with 10 ml of preparation A, three with 10 ml of preparation B (3 mg/ml protein), and two served as controls. The controls were not inoculated at all. All animals were kept in the same room and same pen during the study. The feed was removed 16–24 hours prior to the administration of the cellular fractions (A and B).

Within 24 hours of inoculation one of the pigs inoculated with preparation B (no. 1681) was dead. Necropsy showed fibrin strings and fluid accumulation in the peritoneal cavity. The thoracic cavity showed fibrin strings and pleuritis.

Several of the remaining pigs (see TABLE 1) were showing respiratory signs 24 hours post inoculation, and all remaining pigs were then sacrificed and necropsied. The results are shown on TABLE 1.

TABLE 1

| Animal | Group | Respiratory Signs | Necropsy Lesions |
|---|---|---|---|
| 1676 | Prep A | coughing, nasal discharge | none |
| 1678 | Prep A | normal | fibrin strings in peritoneal cavity |
| 1679 | Prep A | normal | fibrin strings in peritoneal cavity |
| 1677 | Prep B | labored breathing | fibrin strinqs in peritoneal cavity; fluid accumulation, fibrin strings, lung adhesions in thoracic cavity |
| 1680 | Prep B | normal | fibrin strings in peritoneal cavity |
| 1681 | Prep B | died | fibrin strings in peritoneal cavity; fluid accumulation, fibrin strings and lung adhesions in thoracic cavity |
| 1682 | control | normal | none |
| 1683 | control | normal | none |

Material from the lung of pig 1677 was cultured onto Haemophilus test media (HTM) and blood agar (BA). No growth was seen after 24 hours at 37° C. on either medium, thus demonstrating that the clinical signs were not due to bacterial infection.

Example 3

Toxicity in Vero Cells

For cytotoxicity determination of the preparations, Vero cells were grown in Eagles Minimal Non-Essential amino acid medium (EMNE) medium (Gibco) with 2% bovine calf serum to approximately 80–100% confluence in a 96 well plate. The cell monolayers were washed 2–3 times with EMNE basal media and then preparation C was added in 2-fold dilutions across the plate. The cells were scored for cytotoxicity, i.e., cell rounding, enlargement, lysis, and detachment from the substrate, at regular intervals of 24 hours post inoculation. By 48–72 hours, the culture showed cytotoxicity. Thus, the cellfree extract of the present invention causes cytotoxicity in Vero cells.

Example 4

Mouse Vaccine Efficacy

To evaluate the vaccine potential of the cellfree extract, mice were vaccinated intraperitoneally with 0.2 ml of cell-free extract (3 mg/ml protein) prepared as in Example 1 (serotype 4), Preparation C, mixed 1:1 with either Diluvac Forte (Intervet, BV) adjuvant or saline (no adjuvant). The mice were vaccinated at 0 and 14 days and challenged with *H. parasuis* serotype 4 (homologous challenge) or *H. parasuis* serotype 5 (heterologous challenge) 10 days after the second vaccination. The results are shown on TABLE 2.

TABLE 2

| Group | Vaccine | Challenge | Mortality (dead/challenged) |
|---|---|---|---|
| 1 | cell free extract with Diluvac Forte | Live *H. parasuis*, serotype 4 | 0/10 (0%) |
| 2 | cell free extract in saline | Live *H. parasuis*, serotype 4 | 2/10 (20%) |
| 3 | non-vaccinated | Live *H. parasuis*, serotype 4 | 9/12 (75%) |
| 4 | cell free extract with Diluvac Forte | Live *H. parasuis*, serotype 5 | 2/10 (20%) |
| 5 | cell free extract in saline | Live *H. parasuis*, serotype 5 | 1/10 (10%) |
| 6 | non-vaccinated | Live *H. parasuis*, serotype 5 | 12/12 (100%) |

As seen in Table 2, vaccination with the cellfree extract of the present invention provided good protection in mice, even in the absence of an added adjuvant. In addition, the cellfree extract of the present invention, made from serotype 4, provided protection against heterologous challenge of serotype 5, as well as against homologous challenge by serotype 4.

Example 5

Pig Efficacy

To evaluate the vaccine potential of the cellfree extract in pigs, a total of four pigs were vaccinated intramuscularly with 2.0 ml of cellfree extract, prepared as in Example 1 (Preparation C) from serotype 4, mixed 1:1 with Diluvac Forte adjuvant at 3 mg protein per dose. The pigs were vaccinated at 3 and 6 weeks and challenged at 8 weeks with *H. parasuis* serotype 4 (homologous challenge) or *H. parasuis* serotype 5 (heterologous challenge). Controls (14 pigs in each control group) for the study were non-vaccinated animals and whole-cell vaccine groups. The whole cell vaccine contained whole cells from *H. parasuis* serotypes 4 and 5 mixed with Diluvac Forte adjuvant. Each test group was divided in half, with half challenged with serotype 4 and the other half challenged with serotype 5. All animals were sacrificed at 9 weeks and scored according to the following method.

A necropsy score is given to each pig based on the scoring system shown below. A final Necropsy Score is calculated by adding the total points scored. Group Necropsy Scores are calculated by taking the sum of individual pig Necropsy Scores, and dividing by the number of pigs in the group. All pigs that die pre-sacrifice and have typical signs of *H. parasuis* infection at necropsy receive a necropsy score of 25 points.

1. Peritoneal Cavity
   0=normal
   1=fibrin strings present
   2=fluid accumulation
   2=fibrin tag accumulation
   5=adhesion of membranes and/or organs to each other or body wall
2. Thoracic Cavity
   0=normal pleura and pericardium
   2=fluid accumulation
   2=fibrin tag accumulation
   2=pleuritis
   3=pericarditis Necropsy scores are out of a possible 19 (maximum possible points of pigs surviving). The results are shown on TABLE 3.

TABLE 3

| Vaccine | Average Necropsy Score | |
| --- | --- | --- |
| | sero 4 challenge | sero 5 challenge |
| cell free extract Sero 4 | 3.00 | 5.50 |
| whole cell 4 and 5 | 6.43 | 4.57 |
| non-vaccinated | 15.57 | 9.40 |

Table 3 shows that vaccination with the cellfree extract preparation provides good protection against homologous and heterologous challenge in pigs.

Example 7
Protein Characteristics of the Cellfree Extract
A. SDS-PAGE Gels

The cellfree extract preparations (Preparation C, Example 1) were run on SDS-polyacrylamide gels (SDS-PAGE), along with purified outer membrane proteins (OMP) of serotypes 4 and 5. Protein content was determined by the BCA method (Pierce). The results are shown on FIG. 1.

The materials loaded are as follows:
lane 2—Cellfree Extract, 7.25 µg;
lane 3—molecular weight standards;
lane 4—Cellfree Extract, 7.25 µg;
lane 5—45 Kd marker;
lane 6—rainbow markers;
lane 7—molecular weight standards;
lane 8—OMP, serotype 4, 8 µg;
lane 9—rainbow markers;
lane 10—45 Kd marker;
lane 11—molecular weight standards;
lane 12—OMP, serotype 5, 7.6 µg; and
lane 13—rainbow markers.

(Rainbow markers are pre-stained color markers in which different size bands are of different color.)

B. Size Determinations:

To determine the size of any toxins in the cellfree extract, the cellfree extract was filtered through 100 Kd and 300 Kd Amicon filters. The filtrates and retentates were applied to Vero cells and swine alveolar macrophages in 2-fold dilutions, in order to look for cytotoxicity. In addition, 17 ml of the cellfree extract was ultracentrifuged at 28,000 g for 5 hours and applied to Vero cells and swine alveolar macrophages in 2-fold dilutions. None of the cellfree extract preparations had any effect on macrophages. On the Vero cells the 100 kD and 300 kD retentates showed cytotoxicity, as did the ultrasupernatant. Thus, the entity with the toxic activity in the cellfree extract, or toxic functional aggregates thereof, must be larger than 300 kD.

C. Assessment of Hydrophobicity by Adsorption to Phenyl Sepharose Beads

The effect of phenyl SEPHAROSE adsorption of the cellfree extract was evaluated. The initial study was done with phenyl SEPHAROSE beads in a batch method where the cellfree extract was added to beads and then the beads were centrifuged. The supernatant was given to pigs and tested on Vero cells. The second study was performed using a phenyl SEPHAROSE bead column, where the filtrate (unbound), and the eluent (bound) were given to pigs. The scores in the tables below are based on the necropsy scores set forth above.

Pig Scores
Experiment 1

| Test Material | Pig 1 Score | Pig 2 Score | Mean |
| --- | --- | --- | --- |
| Supernatant of Phenyl SEPHAROSE Batch Treatment | 2 | Not Done | 2 |
| Cell Free Extract Positive Control | 6 | 6 | 6 |

Experiment 2

| Treatment | Pig 1 Score | Pig 2 Score | Mean |
| --- | --- | --- | --- |
| Phenyl SEPHAROSE Column - Unbound | 0 | 4* | 2 |
| Phenyl SEPHAROSE Column - Bound and Eluted with Tween | 2 | 2 | 2 |
| Cell Free Extract Positive Control | 4 | 2 | 3 |

*At necropsy, this pig had pus in its lung indicating an underlying infection that was not related to the study. Therefore, the lesions seen may not be due to the HpTx treatment.

Vero Cell Cytotoxicity

| Test Material | Titer |
| --- | --- |
| Supernatant of Phenyl SEPHAROSE Batch Treatment | <2 |
| Cell Free Extract Positive Control | 8 |

D. Effect of Proteinase K Digestion on Toxicity of the Cellfree Extract

The cellfree extract was subjected to digestion with Proteinase K in calcium chloride. The toxicity of the digested cellfree material and CaCl$_2$ controls was tested in pigs.

Pig Scores

| Treatment | Pig 1 Score | Pig 2 Score | Mean |
| --- | --- | --- | --- |
| Proteinase K Digestion | 1 | 1 | 1 |
| CaCl$_2$ Control with Cell Free Extract | 2 | 10 | 6 |

We claim:
1. A cell free, immunogenic extract of *Halmophilus parasuis* serotype 4 obtained from a lysate of said *H. parasuis*, wherein the extract contains a proteinaceous substance having Verocytotoxic activity and the extract is effective for protecting an animal against challenge by *H. parasuis*.

2. A composition comprising the extract of claim 1 and a pharmaceutically acceptable carrier.

3. A vaccine or immunogenic composition for protecting an animal against challenge by *H. parasuis*, comprising a cell free, immunogenic extract of *H. parasuis* serotype 4 obtained from a lysate of said *H. parasuis*, wherein the extract contains a proteinaceous substance having Verocytotoxic activity and the extract is effective for protecting the animal against challenge by *H. parasuis*.

4. The vaccine or immunogenic composition of claim 3, further comprising a pharmaceutically acceptable carrier.

5. The vaccine or immunogenic composition of claim 4, further comprising an adjuvant.

6. A method for protecting an animal against challenge by *H. parasuis*, comprising administering to the animal the extract of claim 1.

7. The method of claim 6, wherein the extract is administered in the presence of an adjuvant.

8. A test kit comprising the cell free extract of claim 1.

* * * * *